United States Patent [19]

Bartos

[11] Patent Number: 4,971,050
[45] Date of Patent: Nov. 20, 1990

[54] OPEN CIRCUIT EMERGENCY BREATHING APPARATUS AND PRESSURE DEMAND VALVE THEREFOR

[75] Inventor: Josef A. Bartos, Diamond Bar, Calif.

[73] Assignee: Respirator Research Ltd., Willoughby, Ohio

[21] Appl. No.: 116,038

[22] Filed: Nov. 3, 1987

[51] Int. Cl.[5] ............................................. A61M 16/00
[52] U.S. Cl. ........................... 128/204.18; 128/204.26; 128/205.24
[58] Field of Search .................... 128/200.24, 204.18, 128/204.22, 204.23, 204.24, 204.26, 204.27, 204.28, 204.29, 205.24

[56] References Cited

U.S. PATENT DOCUMENTS

| | | | |
|---|---|---|---|
| 2,117,952 | 5/1958 | Gordou | 128/202 |
| 2,951,494 | 9/1960 | Holmes | 137/64 |
| 3,097,638 | 7/1963 | Streimer | 128/207 |
| 3,783,891 | 1/1974 | Christianson | 128/204.26 |
| 4,041,978 | 8/1977 | Leeman | 128/204.26 |
| 4,094,314 | 6/1978 | Le Cornec | 128/204.26 |
| 4,186,735 | 2/1980 | Henneman | 128/201.25 |

FOREIGN PATENT DOCUMENTS 1247868  7/1967  Fed. Rep. of Germany .
485981  10/1953  Italy .

*Primary Examiner*—Max Hindenburg
*Assistant Examiner*—John P. Lacyk
*Attorney, Agent, or Firm*—Body, Vickers & Daniels

[57] ABSTRACT

Open circuit emergency breathing apparatus is disclosed which includes a pressure demand valve selectively connectable to primary and secondary sources of breathing gas under pressure to direct breathing gas to a breathing hose attached to the valve and then to a face mask worn by a user of the apparatus. The pressure demand valve includes a diaphragm actuated flow control member and a tubular breathing gas sensor operable in response to inhaling and exhaling by the user to control displacements of the diaphragm and corresponding displacements of the flow control member in a manner which enables obtaining and maintaining the flow of appropriate volumes of breathing gas to the user of a wide range of low to high breathing rates and a wide range of breathing gas supply pressures.

60 Claims, 8 Drawing Sheets

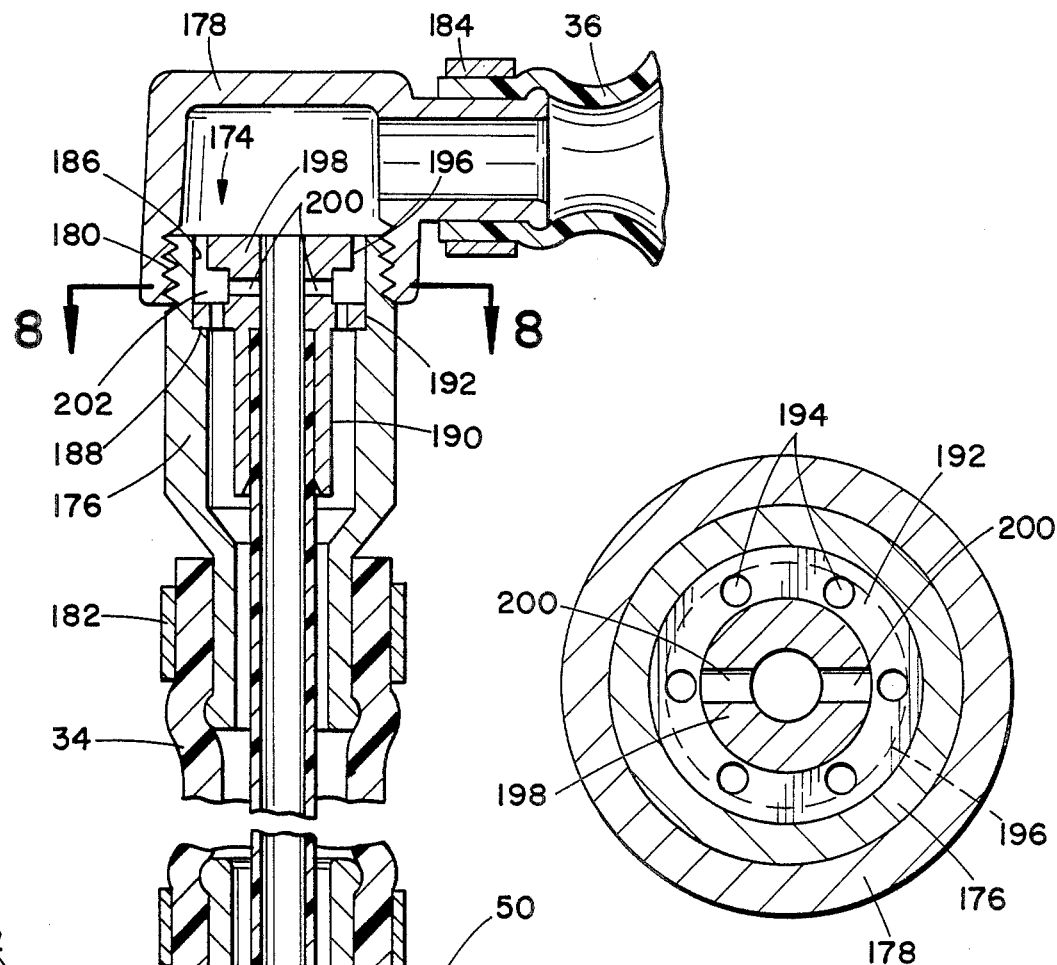
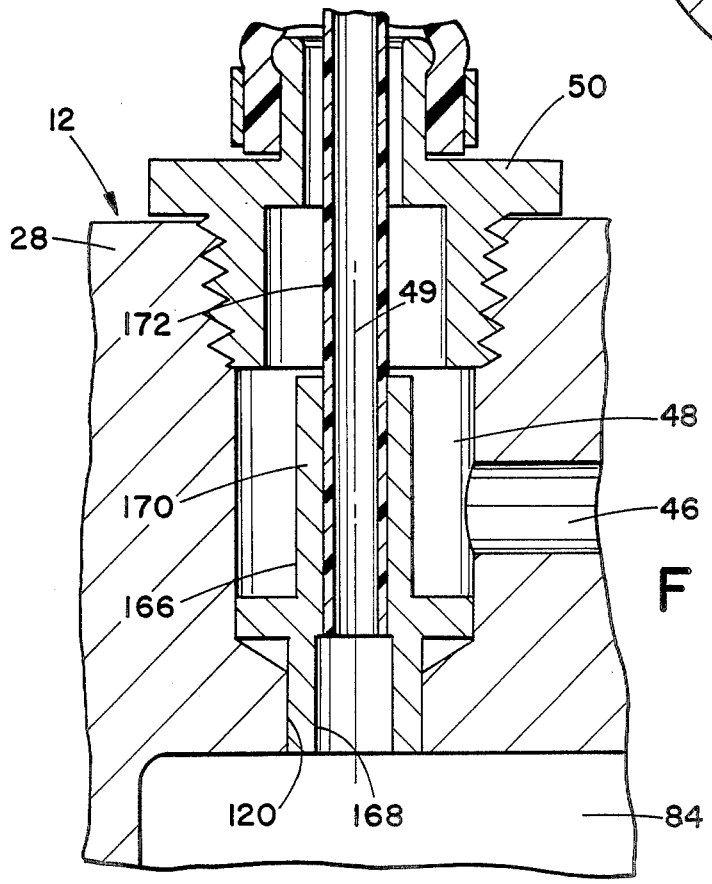
FIG. 8
FIG. 7

OPEN CIRCUIT EMERGENCY BREATHING APPARATUS AND PRESSURE DEMAND VALVE THEREFOR

BACKGROUND OF THE INVENTION

The present invention relates to the art of open circuit emergency breathing apparatus of the character including a pressure demand valve and, more particularly, to an improved pressure demand valve and control arrangements for supplying breathing gas from a source to a user.

The present invention finds particular utility in connection with open circuit emergency breathing apparatus of the character which is known as a supplied air system with an escape feature. More particularly, such apparatus is intended to be connected to a primary supply of breathing gas under pressure in a location where the apparatus is to be used, such breathing gas supply being from an air compressor for example. Generally, a supply hose of considerable length, such as 50 feet for example, connects the primary supply with the breathing apparatus to enable the user to work in a large area in the locale. The emergency breathing apparatus is also adapted to be connected to a secondary source of breathing gas under pressure in a container carried or worn by the user. The second source enables disconnection of the apparatus from the primary source and provides the user with a sufficient supply of breathing gas to enable the user to escape from or evacuate the area in which he or she was working. Such a secondary supply container generally provides a 5 to 10 minute supply of breathing gas for such purpose. In either instance, the breathing gas is supplied to a user, such as by a face mask worn by the user, and the breathing gas inhaled by the user is exhaled to atmosphere from the face mask. Further, the breathing gas is supplied to the face mask through a pressure demand valve which is responsive to the user's rate of inhaling and exhaling, or breathing rate, so as to provide the appropriate flow of breathing gas to the user to meet the latter's needs as determined by such breathing rate.

As is well known, the breathing rate of the user of such emergency breathing apparatus, measured for example in breaths per minute, can vary considerably during use in response for example to increases and decreases in the user's physical exertion. The pressure demand valve, therefore, must be capable of supplying the appropriate volume of breathing gas upon each inhalation of the user regardless of the time of and the time between succeeding inhalations. The volume of breathing gas required by the user, known as the tidal volume, is that volume of breathing gas required to fill the user's lungs when he or she inhales and, accordingly, is dependent on lung capacity and the extent to which the user inhales relative to his or her lung capacity. At low breathing rates, of about 15 or 20 breaths per minute for example, such as when the user is not undergoing significant physical exertion, the time required for one inhaling and exhaling cycle is relatively long and the volume of air inhaled per breathing cycle is relatively higher in comparison with the cycle time and volume per cycle inhaled when the user is undergoing some physical exertion and is breathing at a medium rate of, for example, 20 to 30 breaths per minute. In the latter situation, the time of each breathing cycle and the volume of breathing gas inhaled each breathing cycle decreases. When the user is undergoing considerable physical exertion and is breathing at a high rate of, for example, 30 to 45 breaths per minute the breathing cycle time further decreases as does the volume of breathing gas inhaled each breathing cycle. Accordingly, in connection with emergency breathing apparatus, it will be appreciated that the pressure demand valve must respond to such variations in the breathing rate and volume inhaled per breathing cycle to assure that the user of the apparatus has the required supply of breathing gas at the face mask, to assure that the supply is at a uniform flow rate at any given breathing rate, and to assure that the pressure in the face mask is maintained above atmospheric pressure so that the inhaling portion of the user's breathing cycle does not draw ambient air into the face mask. Furthermore, in connection with supplied air escape type breathing apparatus, the pressure demand valve must be capable of performing in the foregoing manner over a wide range of breathing gas supply pressures. In this respect, breathing gas supplied by the primary source is at a fixed pressure, but from one location to another the pressure may vary from 35 psi to 135 psi, for example. The pressure of breathing gas in the secondary supply container providing the escape source is fixed through a pressure reducing valve associated with the supply container and, generally, is between 120 psi and 135 psi.

Pressure demand valves for use with open circuit type emergency breathing apparatus generally include a diaphragm actuated flow control valve which opens and closes in response to inhaling and exhaling by the user such that breathing gas from the source flows to the face mask worn by the user during inhaling and stops during exhaling. Such pressure demand valves heretofore provided for use with open circuit type emergency breathing apparatus have most often been mounted on the face mask, and there are a number of disadvantages of such a mounting arrangement which either limit acceptability of the equipment and/or endanger the safety of the user and impair the efficiency of the latter in connection with his or her efforts to perform work while wearing the face mask. More particularly in this respect, mounting of a pressure demand valve on the face mask requires the use of plastic materials in connection with the construction of the valve in order to minimize the discomfort to the wearer of the mask as a result of the weight of the valve. Plastic materials undesirably subject the valve to damage and possible inoperativeness by impacting of the valve against objects during use and/or storage of the face mask. Further, the location of the valve on the face mask undesirably limits and/or obstructs visibility of the user, especially in connection with the user's looking downward while wearing the mask In addition to the foregoing disadvantages, pressure demand valves heretofore provided for use with supplied air escape apparatus have not been effective to provide a uniform rate of breathing gas flow to the user's face mask in connection with the variables referred to above with respect to the user's breathing rate, tidal volume requirements, and the pressure of the breathing gas supply. More particularly in this respect, the pressure demand valve has a valve controlled orifice of given size which determines the volume of breathing gas which can flow through the valve to the face mask, and the pressure demand valves heretofore provided have been mounted on the face mask at least in part for the purpose of providing the response time necessary to assure the appropriate supply of breathing gas therethrough to the user in response to varying breathing rates and tidal volumes. Such previous pressure demand valves operate with acceptable effectiveness when the breathing gas supply pressure is relatively high and, for example, above 60 psi. At lower supply pressures, however, the pressure demand valves cannot operate effectively unless the valve actuating diaphragm and flow orifice are enlarged to enable the necessary volume of flow thereacross to the user. It will be appreciated that to enlarge the diaphragm of a face mask mounted pressure demand valve would further add to the weight and visibility problems mentioned above.

SUMMARY OF THE INVENTION

In accordance with the present invention, improved open circuit emergency breathing apparatus is provided including an improved pressure demand valve and control arrangements therefor by which the foregoing and other disadvantages of such valves heretofore provided are minimized or overcome. More particularly in this respect, a pressure demand valve according to the present invention is advantageously separate from the face mask of the breathing apparatus and is adapted to be worn on the body of a user such as by means of a belt or body strap. Alternatively, the pressure demand valve is adapted to be connected to the valved outlet of a breathing gas container providing an escape source of breathing gas and which is worn by the user such as by means of a belt or body strap. The pressure demand valve preferably has two separate breathing gas supply connections, one of which is adapted to be connected to the valved outlet of the escape supply container, and the other of which is adapted to be coupled with the supply hose from the primary breathing gas supply. The demand valve further includes an outlet adapted to be connected to a face mask by means of a breathing hose. In any event, the pressure demand valve is separate from the face mask, whereby the user is not encumbered with the weight thereof on the mask and/or subjected to restricted visibility resulting therefrom. Additionally, by removing the pressure demand valve from the face mask, the valve housing can if desired be constructed from metal so as to provide maximum protection against damage thereto during use and/or storage of the apparatus.

The pressure demand valve includes a diaphragm actuated flow control valve element for opening and closing the valve port or orifice which determines the volume of flow through the valve to the face mask. Opening and closing of the valve element is in response to displacements of the diaphragm in opposite directions relative to a neutral diaphragm position, and such diaphragm displacements are in response to inhaling and exhaling by the user. The flow control valve element is slightly open in the neutral position of the diaphragm, and the diaphragm is biased toward the neutral position when the valve port is closed during exhalation so as to open the valve prior to termination of exhaling and thus maintain a positive pressure in the face mask at all times during use of the apparatus. Further in accordance with the present invention, separation of the pressure demand valve from the face mask and control of the valve to achieve uniform and desired flow rates of breathing gas therethrough to the user in response to variable breathing rates and with a supply pressure from about 35 psi to 135 psi, are enabled through the provision of breathing sensor arrangements communicating the diaphragm control chamber with the face mask. Breathing gas flowing through the valve from the source is precluded from entering the diaphragm control chamber by the sensor arrangements, and the latter and are responsive to inhaling and exhaling of the user to control the pressure in the diaphragm chamber and thus displacements thereof.

It is accordingly an outstanding object of the present invention to provide improved open circuit emergency breathing apparatus including improved pressure demand valve arrangements for controlling the flow of breathing gas from a source under pressure to a user of the apparatus.

A further object is the provision of apparatus of the foregoing character in which the pressure demand valve is adapted to be selectively connected to primary and secondary sources of breathing gas under pressure.

Another object is the provision of apparatus of the foregoing character in which the pressure demand valve is separate from the face mask or other user utilization device of the breathing apparatus and is adapted to be selectively worn on the body of the user or connected to the outlet of a valved breathing gas container supportable on the body of the user.

Still another object is the provision of apparatus of the foregoing character in which the pressure demand valve is controlled such as to provide uniformity with respect to flow rates of breathing gas therethrough over a wide range of breathing rates of the user and over a wide range of low to high breathing gas supply pressures.

Yet another object is the provision of breathing apparatus and a pressure demand valve of the foregoing character wherein the flow of breathing gas through the pressure demand valve is across a valve port adapted to be closed and opened by a flow control valve element actuated by a pressure responsive diaphragm, and wherein the displacements of the diaphragm are controlled by breathing sensor arrangements between the diaphragm chamber and face mask and responsive to inhaling and exhaling of the user of the apparatus.

Yet a further object is the provision of a pressure demand valve of the foregoing character wherein the flow control valve element is displaced by the diaphragm through a lever arrangement and wherein the diaphragm is biased to open the valve element prior to termination of the user's exhaling whereby, together with sensor control of the diaphragm in response to inhaling and exhaling, a more uniform flow of breathing gas to the user and positive pressure in the face mask are achieved than heretofore possible and are achieved in response to varying breathing rates of the user and various breathing gas supply pressures.

Still a further object is the provision of a pressure demand valve of the foregoing character which is economical to construct, convenient to use and to incorporate as a component part of emergency breathing apparatus of the character providing a user with supplied air and escape capabilities and which, in use, is reliable and efficient so as to promote both safety and comfort for a user of the apparatus.

BRIEF DESCRIPTION OF THE DRAWINGS

The foregoing objects, and others, will in part be obvious and in part pointed out more fully hereinafter in conjunction with the written description of preferred embodiments of the invention illustrated in the accompanying drawings in which:

FIG. 3A is an enlarged sectional elevation view of the flow control valve as seen in FIG. 3;

FIG. 7 is a sectional elevation view of a portion of the pressure demand valve shown in FIGS. 1-6 and showing another embodiment of the sensor arrangement for controlling the valve;

FIG. 8 is a cross-sectional view taken along line 8—8 in FIG. 7; and,

DESCRIPTION OF PREFERRED EMBODIMENTS

Figure 1:
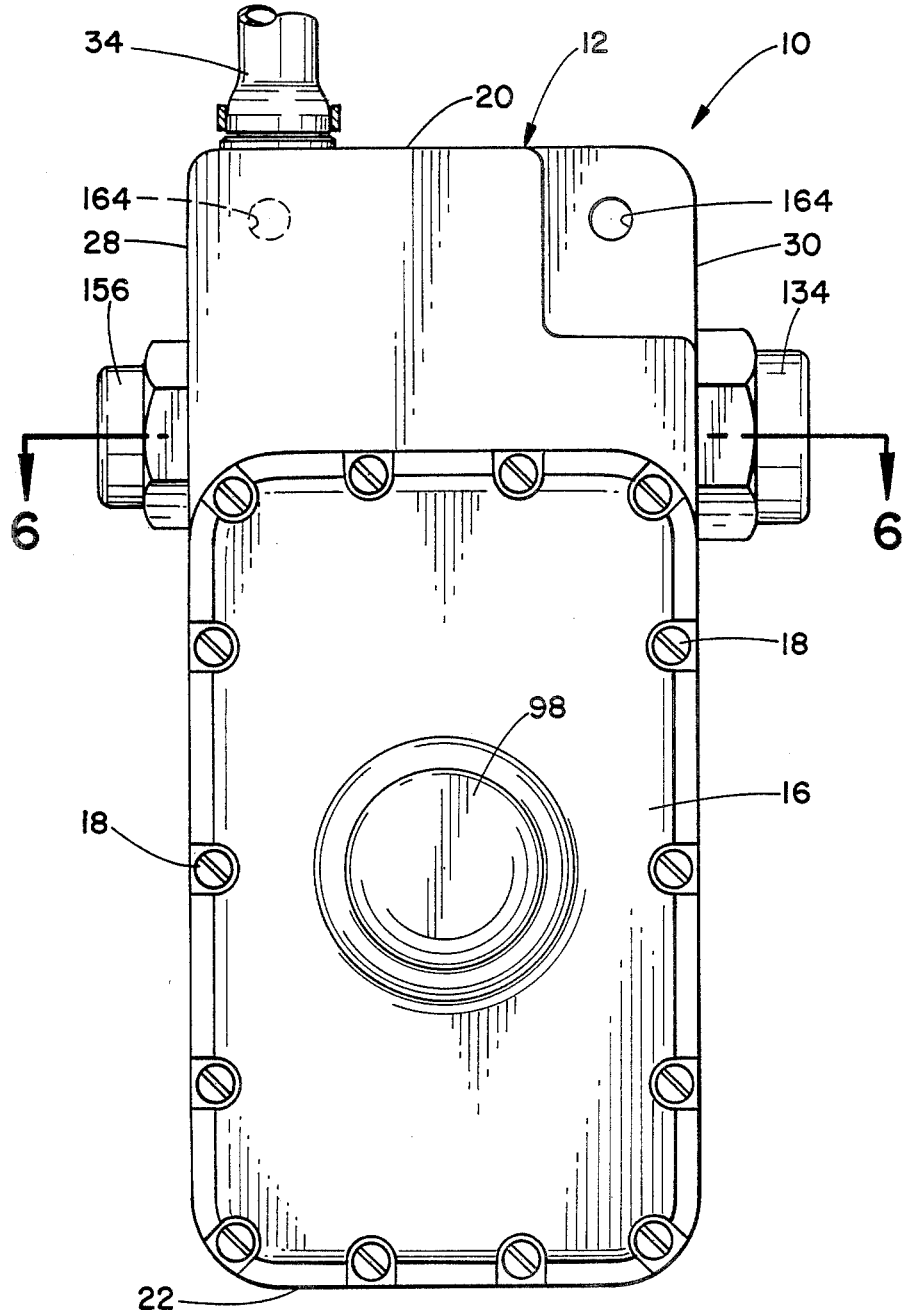
FIG. 1 is a front elevation view, partially in section, of emergency breathing apparatus including a pressure demand valve in accordance with the present invention.
Figure 2:
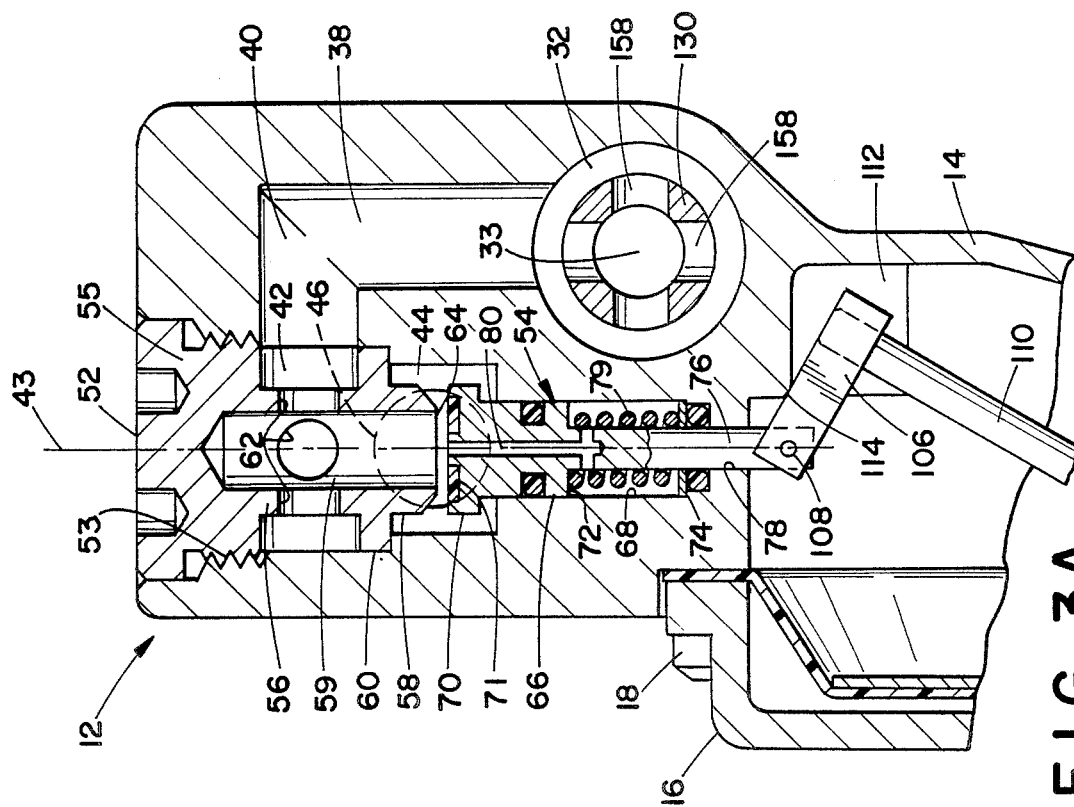
FIG. 2 is a plan view of the pressure demand valve.

Referring now in greater detail to the drawings wherein the showings are for the purpose of illustrating preferred embodiments of the invention only and not for the purpose of limiting the invention, a pressure demand valve 10 is shown in FIGS. 1-6 which is comprised of a housing having a body portion 12 and a lower portion defined by a pan-shaped wall 14 integral with and depending from body portion 12 and a pan-shaped cover wall 16 suitably secured to the lower end of body portion 12 and to wall 14 such as by means of threaded fasteners 18. The housing is generally rectangular in configuration and has a top 20, a bottom 22, a front end 24, a back end 26 and laterally opposite sides 28 and 30. Body portion 12 of the housing is provided with a laterally extending circular bore 32 having an axis 33. Bore 32 opens through sides 28 and 30 of the body portion and, as described more fully hereinafter, facilitates connecting the pressure demand valve to a source of breathing gas under pressure. Body portion 12 further includes a breathing gas flow passageway therethrough for directing breathing gas from the source to a user through a user utilization arrangement which, in the embodiment disclosed is comprised of a breathing hose 34 connected to a face mask as partially shown in FIG. 1 and designated by the numeral 36. The breathing gas flow passageway includes an inlet end defined by a bore 38 opening into bore 32 and extending upwardly therefrom, and a bore 40 extending forwardly in a body portion 12 from the upper end of bore 38. The breathing gas flow passageway further includes a vertical, cylindrical passageway portion comprising an upper bore 42 having an axis 43 and a coaxial lower bore 44, and bore 40 of the inlet end of the flow passageway opens into upper bore 42. The breathing gas flow passageway further includes an outlet end defined by a bore 46 opening into and extending laterally from lower bore 44, and a bore 48 extending upwardly from the laterally outer end of bore 46 and through top 20 of the body portion. Bore 48 has an axis 49 and provides an outlet port to which breathing hose 34 is connected by means of a suitable fitting 50.

Pressure demand valve 10 further includes a flow control valve between the inlet and outlet ends of the breathing gas passageway therethrough and, in the embodiment illustrated, the flow control valve is in the vertical passageway portion defined by bores 42 and 44 and is provided by a valve seat insert member 52 and a vertically reciprocal valve element 54. Valve seat insert 52 includes a body portion 53 threadedly interengaged with a threaded bore 55 in body portion 12 above bore 42. The insert further includes upper and lower tubular wall portions 56 and 58, respectively, extending downwardly from body portion 53 coaxial with axis 43 of bores 42 and 44 and providing a cylindrical passage 59 in the insert. A radially outwardly extending flange 60 between walls 56 and 58 engages a shoulder between bores 42 and 44, not designated numerically, and sealingly engages with the cylindrical wall of bore 42 and the shoulder to sealingly separate bores 42 and 44 with respect to the flow of breathing gas therebetween around flange 60. Upper tubular wall portion 56 of the valve seat insert is disposed in upper bore 42 and is provided with a plurality of openings 62 radially therethrough communicating passage 59 with upper bore 42 and thus the inlet end of the breathing gas passageway. Lower tubular wall portion 58 of the insert is disposed in lower bore 44 and has a tapered lower edge 64 providing a valve seat for valve member 54.

As best seen in FIG. 3A, valve member 54 includes a cylindrical body portion 66 vertically slidably supported in a cylindrical chamber 68 coaxial with axis 43. Body portion 66 includes an annular flange 70 at the upper end thereof provided with an annular seal member 71 which is adapted to engage against seat 64 to close the breathing gas flow passageway and to be displaced downwardly away from seat 64 to open the breathing gas passageway for the flow of breathing gas therethrough from the source to the user. Passage 59 in valve seat insert 52 is slightly smaller in diameter than chamber 68 and body portion 66, for the purpose set forth hereinafter, and flange 70 on the valve member has a diameter somewhat larger than that of passage 59 and body portion 66. Body portion 66 of valve member 54 has a lower end 72 in chamber 68 and spaced from the bottom wall 74 of chamber 68 when the valve element is in its closed and opened positions, and the valve member further includes a stem 76 extending downwardly from lower end 72 and through an opening 78 into the diaphragm chamber of the pressure demand valve to be described hereinafter. A biasing spring 79 surrounds stem 76 between lower end 72 of the valve member and bottom wall 74 of chamber 68 and biases valve member 54 toward the closed position thereof. Preferably, valve member 54 is pressure biased in the closing direction thereof and, for this purpose, the valve member is provided with a port 80 extending downwardly therethrough from upper end 70 into stem 76 and thence laterally so as to open into chamber 68 between inner end 72 of body portion 66 and bottom wall 74 of the chamber. Breathing gas under pressure is therefore adapted to flow through port 80 and into chamber 68, and this provides a biasing pressure on the underside of the valve member which, together with spring 79, maintains the valve closed against the pressure of supply gas against the upper end thereof and promotes closing of the valve member from its open position as explained more fully hereinafter. While not designated numerically, it will be appreciated from the drawings that appropriate seals, such as O-ring seals, are provided between valve member 54 and chamber 68 and between stem 76 and opening 78 to seal against the flow of breathing gas across the sealed surfaces.

Walls 14 and 16 of the housing provide a diaphragm chamber, and a displaceable diaphragm assembly 82 having an axis 83 mounted on the housing to divide the diaphragm chamber into first and second chamber portions 84 and 86, respectively. Diaphragm assembly 82 includes a flexible diaphragm member 88 of elastomeric material having its outer periphery clampingly engaged between opposed peripheral portions of walls 14 and 16 and the lower end of body 12. The diaphragm assembly further includes plates 90 and 91 on axially opposite sides of the diaphragm and clamped thereto by a planar clamping plate 92 facially engaging plate 90 and having a tubular wall portion 94 extending through openings therefor in plates 90 and 91 and diaphragm 88 and receiving a clamping ring 96 thereon. Wall 16 of the housing includes a bulbous portion 98 providing a cavity in chamber portion 86 aligned with wall 94, and the cavity and wall 94 together provide support and guidance for a biasing spring 100 which axially biases the diaphragm assembly to a central position in the diaphragm chamber in which the diaphragm 88 is in a vertical plane as shown by the solid line position of the diaphragm assembly in FIG. 3. Chamber portion 86 is vented to atmosphere by means of a port 102 in bulbous portion 98.

As will be described in greater detail hereinafter, diaphragm assembly 82 is axially displaced to the right and left of the central position thereof shown in FIG. 3 during use of the breathing apparatus and in response to inhaling and exhaling by the user. Valve element 54 is displaced between its open and closed positions in response to such displacements of the diaphragm assembly, and the valve element is displaced in the opening direction by a valve member actuating lever 104 in diaphragm chamber portion 84. Lever 104 is L-shaped and includes a short lever are 106 having its outer end pivotally connected to stem 76 of the valve member by means of a pin 108, and a long lever arm 110 rigidly secured to the inner end of arm 106 and having an outer end 110a slidably engaging the planar surface of clamping plate 92. The lower end of body portion 12 of the pressure demand valve which defines the upper region of diaphragm chamber portion 84 is configured to provide a pair of laterally spaced apart guide flanges 112 and a laterally extending edge 114 therebetween, and lever are 106 extends between guide flanges 112 and engages edge 114 which provides a fulcrum edge for pivotal displacements of the lever. Guide flanges 112 preclude lateral displacement of the lever and also precludes pivotal displacement of the lever and thus valve member 54 about axis 43 of the latter.

Figure 3:
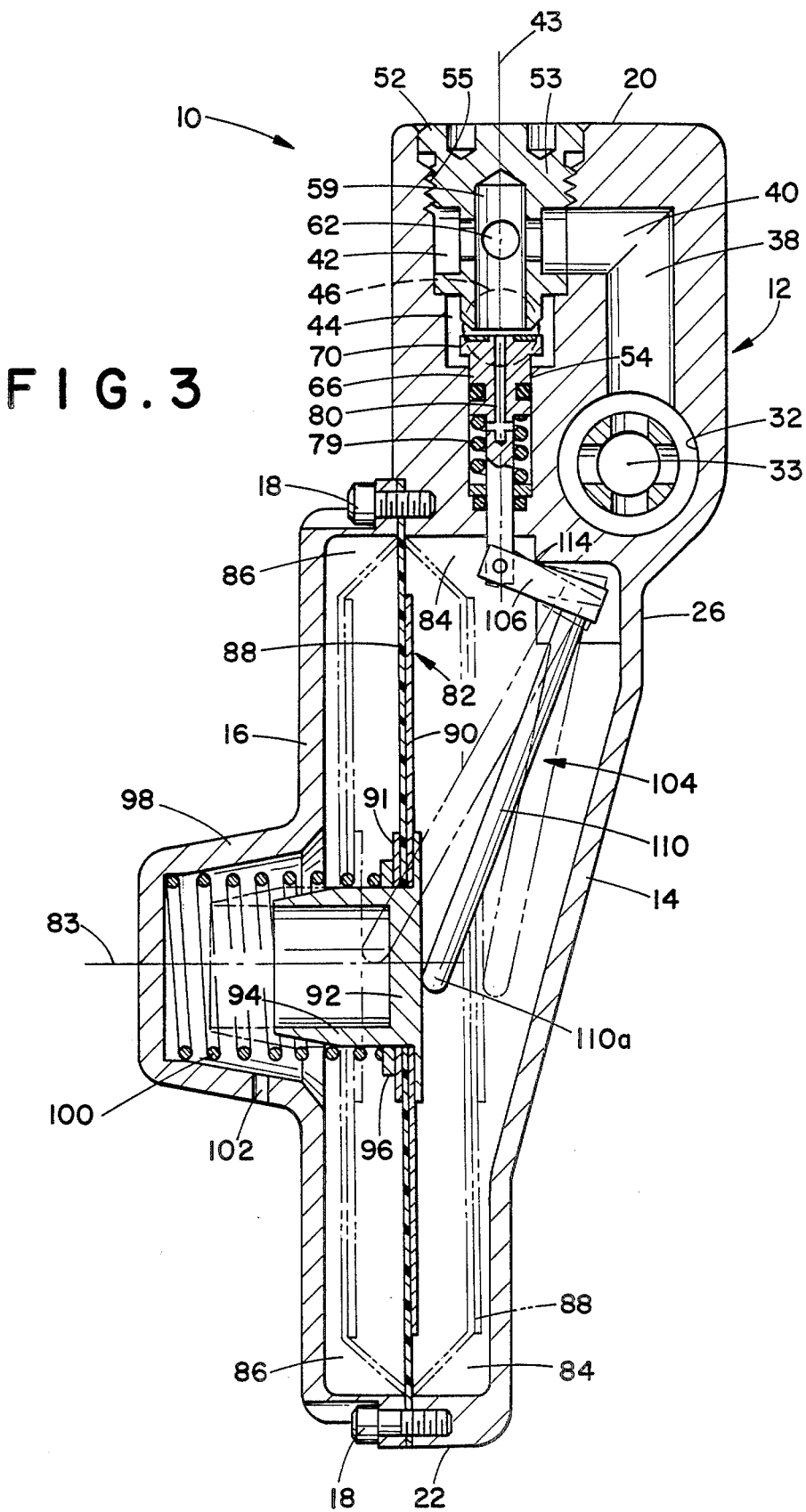
FIG. 3 is a sectional elevation view of the pressure demand valve taken along line 3—3 in FIG. 2.
Figure 4:
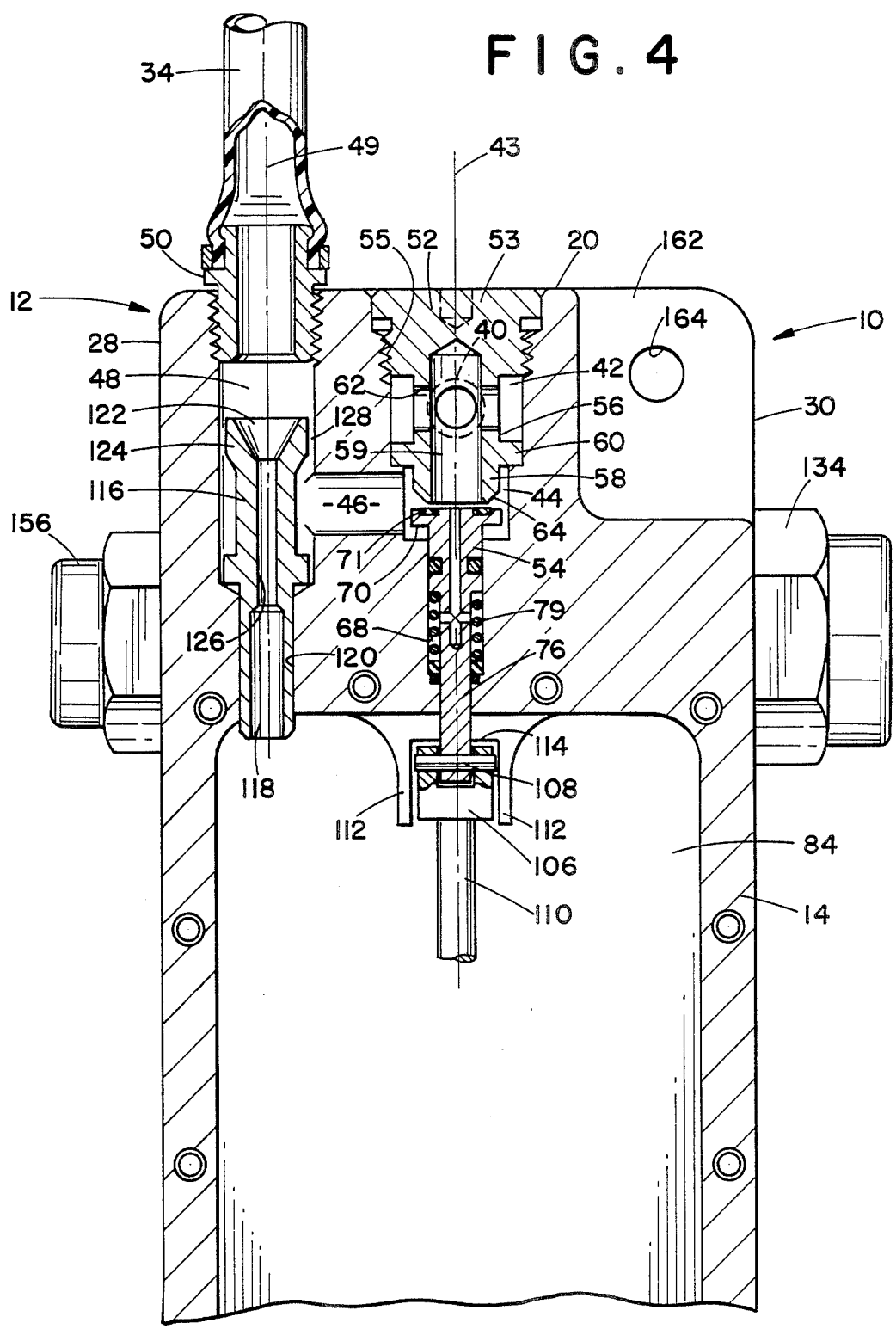
FIG. 4 is a sectional elevation view of a portion of the pressure demand valve taken along line 4—4 in FIG. 2.

As best seen in FIG. 4, the pressure demand valve further includes a breathing sensor which, in the embodiment of FIGS. 1–6, is a tubular member 116 having an inner end 118 press fitted or otherwise secured in a bore 120 in body portion 12 so as to open into diaphragm chamber portion 84. Member 116 further includes an outer end 112 which is coaxial with and located in outlet port 48 of the outlet end of the breathing gas flow passageway through the valve. End 122 faces downstream with respect to the direction of flow of breathing gas from the source across the flow control valve and to the outlet port and, in the embodiment illustrated, includes a conical flange 124 diverging relative to axis 49 and with respect to the downstream direction of flow referred to. Member 116 further includes a restricted passageway or port 126 therethrough, and flange 124 is coaxial with and smaller in diameter than the diameter of outlet port 48 so as to provide an annular space 128 therebetween. Preferably, annular space 128 has an area corresponding to the area of the flow control valve port as defined by the diameter of passage 59 and thus valve seat 64 of insert 52.

Figure 5:
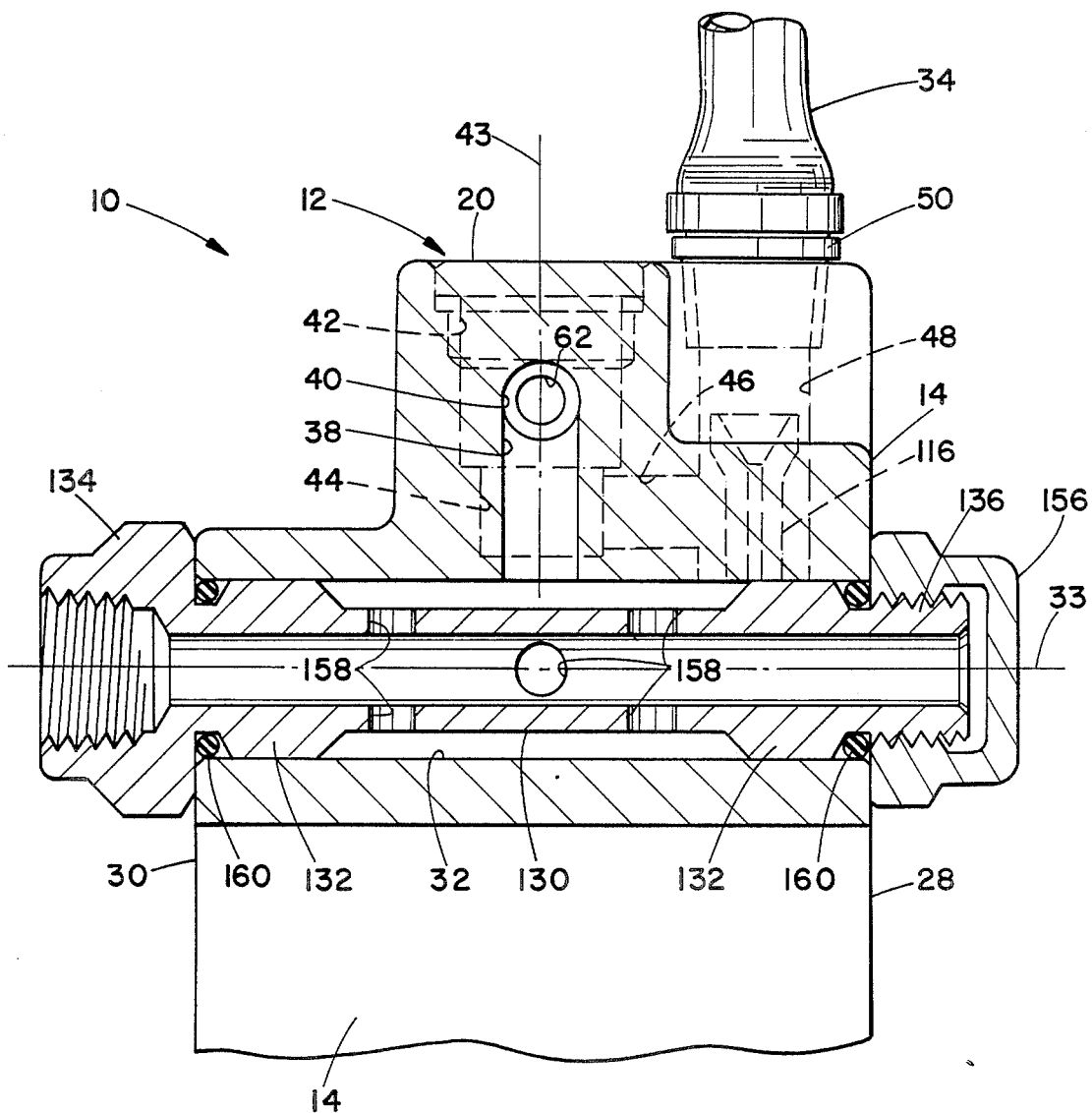
FIG. 5 is a sectional elevation view of the upper portion of the pressure demand valve taken along line 5—5 in FIG. 2.
Figure 6:
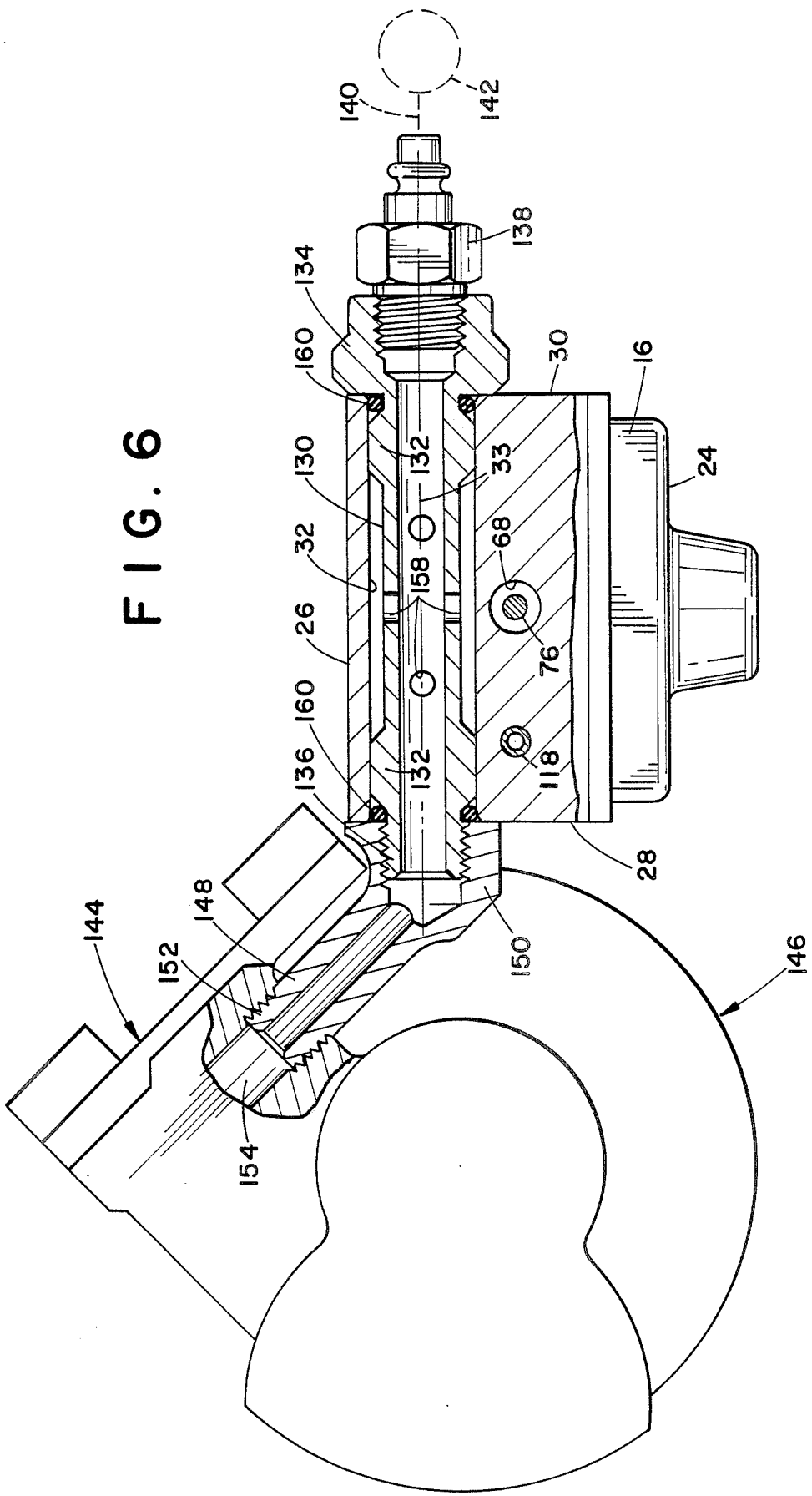
FIG. 6 is a cross-sectional view of the pressure demand valve taken along line 6—6 in FIG. 1 and showing the valve mounted on a pressure regulating valve associated with a breathing gas supply container and further showing the valve connected to a primary source of breathing gas under pressure.

As mentioned hereinabove, the inlet end of the breathing gas flow passageway through the pressure demand valve, as defined by ports 38 and 40, is adapted to be connected to a source of breathing gas under pressure. In accordance with the preferred embodiment, as best seen in FIGS. 5 and 6 of the drawing, such connection is achieved through a coupling sleeve 130 supported in and extending through bore 32 in housing portion 12 in coaxial relationship therewith. Sleeve 130 has a tubular central portion of smaller diameter than the diameter of bore 32 and is provided adjacent the opposite ends of bore 32 with spool portions 132 which engage bore 32 to support sleeve 130 in coaxial relationship therewith. The opposite ends of sleeve 130 extend laterally outwardly of the corresponding side of body portion 12 of the valve housing, and the end of sleeve 130 adjacent housing side 30 is provided with an integral internally threaded coupling portion 134. The end extending outwardly adjacent housing side 28 is provided with an integral externally threaded coupling portion 136. Coupling portion 134 is adapted to be provided with a quick disconnect fitting 138 which, in a well known manner, provides for the quick connecting and disconnecting of the pressure demand valve to a mating coupling on the end of a hose 140 by which the pressure demand valve can be connected with a primary source of breathing gas under pressure 142, as schematically shown in FIG. 6. Such a quick disconnect fitting 138 provides for the corresponding end of sleeve 130 to be closed when disconnected from the line fitting.

Coupling portion 136 facilitates connecting the pressure demand valve to the outlet of a pressure regulating valve 144 having its inlet connected to a breathing gas container 146 which provides a secondary source of breathing gas under pressure. In the embodiment shown, such coupling to the outlet of the pressure reducing valve is by means of an angled fitting 148 having an internally threaded end 150 connected to coupling portion 136 and having an externally threaded end 152 threadedly interengaged with the outlet port 154 of the pressure reducing valve. It will be understood, of course, that the pressure regulating valve includes an on-off flow control valve, not shown, operable when open to provide for the flow of breathing gas from container 146 to outlet port 154 and, when closed, to preclude such flow. The operation of such a pressure regulating valve in connection with an associated supply chamber is well understood by those skilled in the art and the structure and mounting of the valve on the supply container are not important in connection with the present invention. Having a pressure regulating valve and supply container arrangement suitable for use with the present invention is shown in my copending application Ser. No. 932,562, filed Nov. 20, 1986, now U.S. Pat. No. 4,798,203, issued Jan. 17, 1989, entitled Portable Emergency Breathing Apparatus, and the disclosure of which is incorporated herein by reference. The angled fitting 148 shown in FIG. 6 advantageously provides for the portable supply of breathing gas under pressure and the pressure demand valve when attached thereto to have a contour which promotes maintaining the two components close to the body of the user of the breathing apparatus on which they are supported. Suitable arrangements for supporting the pressure regulating valve and supply container on the body of a user are also disclosed in my aforementioned copending application.

It will be appreciated that it is possible to connect pressure demand valve 10 to primary source 142 independent of the attachment of the valve to secondary source 146. In connection with such use, as will be appreciated from FIG. 5, coupling portion 136 is provided with a closure cap 156 which closes the corresponding end of sleeve 130 and axially engages the sleeve in bore 32 against displacement therefrom. Sleeve 130 is provided intermediate spools 132 with a plurality of openings 158 through which supplied air entering either end of the sleeve flows to inlet port 38 of the pressure demand valve, and the axially opposite ends of bore 32 are provided with O-ring seals 160 which seal against the leakage of supplied air across the ends of the bore. When the pressure demand valve is connected to primary source 142 independent of connection to secondary source 146, the pressure demand valve is adapted to be supported of the body of the user such as through the use of a shoulder or body strap. To facilitate such attachment of the pressure demand valve to the body of the user, the upper end of body portion 12 of the valve housing is configured to provide flanges 162 having openings 164 therethrough, as will be appreciated from FIGS. 1 and 2. Openings 164 are adapted to receive suitable body strap or shoulder strap clips, not shown. Further in this respect, openings 164 can be used to attach a waist band or belt receiving component to the valve housing to facilitate the user's wearing the pressure demand valve through the use of a belt or body strap.

It is believed that the following description of the operation of the pressure demand valve shown in FIGS. 1-6 will be readily understood from the foregoing description thereof. Prior to turning on the source of breathing gas under pressure and the user's putting on the face mask, the diaphragm assembly is in the solid position thereof shown in FIG. 3 and in which spring 100 positions diaphragm 88 in a vertical plane as shown. In this position of the diaphragm assembly, upper end 70 of flow control valve member 54 is slightly displaced from valve seat 64, against the bias of spring 79, whereby the flow control valve is partially open. Presuming that the pressure demand valve is connected to primary breathing gas source 142 through line 140 and fitting 138 and that the user has put on face mask 36, breathing gas under pressure flows into sleeve 130 and thence through openings 158 into bore 32 and from bore 32 into the inlet of the pressure demand valve as defined by bores 38 and 40. From bore 40 the breathing gas flows into upper bore 42 and through openings 62 to the interior passage 59 of tubular valve seat insert 52 and thence through portion 80 in valve member 54 to chamber 68. Presuming that the user has initially exhaled after putting on the face mask, such exhaling provides a back pressure through breathing hose 34 and port 126 of breathing sensor member 116 into diaphragm chamber portion 84 such that diaphragm assembly 82 is displaced to the left in FIG. 3 against the bias of spring 100. Such exhaling also provides a back pressure through bores 48, 46 and 44 and thus against the underside of flange 70 of valve member 54. This back pressure together with the pressure in chamber 68 and the bias of spring 79 displaces valve member 54 upwardly to its closed position against seat 64. During the upward displacement of the valve member, lever 104 pivots clockwise about fulcrum edge 114 to follow the diaphragm assembly. Spring 100 operates to dampen the closing movement of valve member 54 to avoid undesirable impacting and/or bouncing thereof relative to seat 64. As the user's exhaling approaches termination, there is a pressure drop in diaphragm chamber 84 across breathing sensor 116. Just prior to termination of exhaling, diaphragm spring 100 in effect anticipates such termination and displaces diaphragm 100 to the solid line position in FIG. 3, whereby lever 104 displaces valve member 54 in the opening direction thereof. Therefore, valve member 54 slightly opens prior to termination of exhaling such that breathing gas under pressure flows across seat 64 into bores 44 and 46 and thence through annular space 128 into outlet bore 48 and breathing hose 34 to the face mask to assure that there is a positive pressure in the face mask at all times during use of the apparatus.

When the user begins to inhale, there is a further pressure drop in diaphragm chamber 84 across breathing sensor member 116, whereby diaphragm assembly 82 is displaced to the right in FIG. 3 from its solid line position to further pivot lever 104 counterclockwise about fulcrum edge 114 to displace valve member 54 toward its fully open position. The position of tubular breathing sensor member 116 relative to bore 46 and outlet bore 48 precludes breathing gas flowing through the valve port to the face mask from entering diaphragm chamber 84 and affecting operation or control of the diaphragm. At the same time, the flow of breathing gas under pressure through space 128 past flange 124 of sensor member 116 produces a venturi effect with respect to bore 126 in the sensor member to accelerate the pressure drop in diaphragm chamber portion 84 as soon as valve member 54 opens and during inhaling. This accelerates displacement of the diaphragm assembly 82 to the far right in FIG. 3 and, accordingly, displacement of valve member 54 toward its fully open position, whereby the desired volume of breathing gas quickly flows through the valve and to the user. When inhalation ceases, back pressure is again effective through port 126 in breathing sensor member 116 to increase the pressure in diaphragm chamber position 84 so as to displace the diaphragm assembly to the left in FIG. 3 from its right hand position, whereupon valve spring 79, the pressure in chamber 68 beneath valve member 54 and back pressure in bores 48, 46 and 44 displace valve member 54 toward seat 64 to close the valve port against the flow of breathing gas thereacross until exhaling approaches termination as described above. During exhalation, restricted passageway 126 in sensor member 116 restricts the back pressure flow into diaphragm chamber 84 so as to dampen and thus control the rate of displacement of diaphragm assembly 82 to the far left position shown in FIG. 3. Such dampening precludes undesirable impacting of the valve member against seat 64, bouncing of the valve member relative to the valve seat and the premature closing of the valve member against the seat. Moreover, such control of the displacement of valve member 54 enables maintaining a synchronism between the user's breathing rate and the opening and closing movements of the valve member which provides for a uniform flow rate and the appropriate volume of flow in response to a wide range of breathing rates.

If the pressure demand valve is connected to a secondary source of breathing gas under pressure as provided for example by container 146 in FIG. 6, such secondary source enables the user to disconnect from the primary source for the purpose of escaping from the area in which he or she is located. As will be appreciated from FIG. 6, a user wanting to avail himself or herself of the escape feature would open the supply container valve whereupon breathing gas under pressure would flow from outlet port 154 of the pressure regulating valve into sleeve 130 and through ports 158 into bore 32, whereupon the user could disconnect line 140 from fitting 138 and proceed to evacuate the area. The pressure demand valve will continue to operate in the manner described hereinabove with the container worn by the user providing the source of breathing gas under pressure.

FIGS. 7 and 8 of the drawing illustrate another embodiment of the breathing sensor arrangement to provide the desired controlled operation described above. The pressure demand valve of this embodiment is of the same structure described hereinabove in connection with FIGS. 1-6. Accordingly, only a portion of the pressure demand valve is shown in FIGS. 7 and 8, and it will be appreciated that the embodiment of the breathing sensor illustrated in the latter Figures is with respect to the structural configuration of the remaining portion of the valve shown in FIGS. 1-6.

Referring now to FIGS. 7 and 8, breathing sensor 116 is replaced by a tubular hose coupling 166 having an inner end 168 press fitted in opening 120 in body portion 12 of the housing and having an outer end 170 extending into outlet port 48. Outer end 170 receives the corresponding end of a flexible sensor tube 172 which extends through breathing hose 34 and is connected a its opposite end to the face mask 36 by means of a coupling member 174. More particularly in this respect, breathing hose 34 is connected to face mask 36 by means of a tubular coupling sleeve 176 and a face mask coupling component 178, which coupling sleeve and face mask components are threadedly interengaged as indicated by numeral 180. Coupling sleeve 176 has an inlet end to which breathing hose 34 is suitably secured such as by a hose clamp 182, and face mask coupling component 178 has an outlet end to which face mask 36 is suitably secured such as by a clamp 184. The interior thereof is axially recessed to provide a cylindrical inner wall 186 and a radially extending peripheral shoulder 188 at the axially inner end of wall 186. Coupling member 174 includes a tubular inner end 190 receiving the corresponding end of sensor tube 172, and a radially outwardly extending flange 192 intermediate the opposite ends thereof and which engages against shoulder 188 and has a press fit with wall 186 so as to be axially secured in place in coupling 176.

Flange 192 is provided with a plurality of openings 194 circumferentially spaced apart thereabout and extending axially therethrough, and the total area provided by the openings 194 is at least equal to the area of the valve port in the pressure demand valve. The upper end of coupling member 174 has a radially outwardly extending circumferential flange 196 which has a circular outer periphery providing an annular gap with wall 186 and which gap has an area equal to the area of the valve port in the pressure demand valve. The circular contour of the outer periphery of flange 196 is shown by broken lines in FIG. 8 to illustrate the relationship between the flange and wall 186 by which the foregoing gap is established. Flange 196 is axially spaced downstream from flange 192 with respect to the direction of flow of breathing gas from the source to the user, and the tubular wall portion 198 of the coupling member 174 axially between flanges 192 and 196 is provide with a pair of diametrically opposed openings 200 therethrough communicating the area 202 immediately behind flange 196 with the interior of the coupling member. Flange 192 primarily serves to position coupling member 174 coaxial with the interior of tubular hose coupling 176, and it will be appreciated that other arrangements could be provided for obtaining such support. It is only important in connection with such support that the area of openings 194 thereacross is at least equal to the area of the valve port in the pressure demand valve.

Operation of the pressure demand valve with the breathing sensor illustrated in FIGS. 7 and 8 is the same as that described hereinabove in connection with the embodiment shown in FIGS. 1-6. In this respect, during the use of the modified breathing apparatus, it will be appreciated that columns of breathing gas are in sensor tube 172 and breathing hose 34, whereby there is a pressure drop in the diaphragm chamber as exhalation approaches termination and upon which pressure drop the diaphragm spring displaces the diaphragm to initially open the valve before exhaling terminates so as to maintain positive pressure in the face mask at all times during use of the apparatus. Sensor tube 172 precludes the flow of breathing gas from the source into the diaphragm chamber, and as exhaling terminates and inhaling begins the pressure drop in the diaphragm chamber increases so as to displace the diaphragm assembly and the flow control valve element further away from valve seat 64 toward its fully open position. The flow of breathing gas through breathing hose 34 to the face mask is across the gap between flange 196 of coupling member 174 and cylindrical wall 186 of the breathing hose coupling. This flow causes a venturi effect in the sensor tube to accelerate the pressure drop in the diaphragm chamber and thus accelerate displacement of the diaphragm assembly and opening displacement of valve member 54. During inhaling and exhaling there is a restriction to flow relative to diaphragm chamber portion 84 resulting from the length and internal diameter of sensor tube 172. In connection with exhalation, this restriction to flow provides the same function as the restricted passage 126 through sensor member 116 with respect to controlling the rate of pressure increase in diaphragm chamber portion 84 so as to preclude premature closing as well as impacting or bouncing of the valve member against the valve seat during closure of the valve. Openings 200 have a total area of about one-third the area of the valve port and serve to dampen the venturi effect by directing a portion of the flow of breathing gas into the coupling member during inhalation. While openings 200 serve this purpose in connection with a gap which equals the area of the valve port, the same effect can be achieved by increasing the area of the gap so that the latter is about one-third larger than the area of the valve port.

Figure 9:
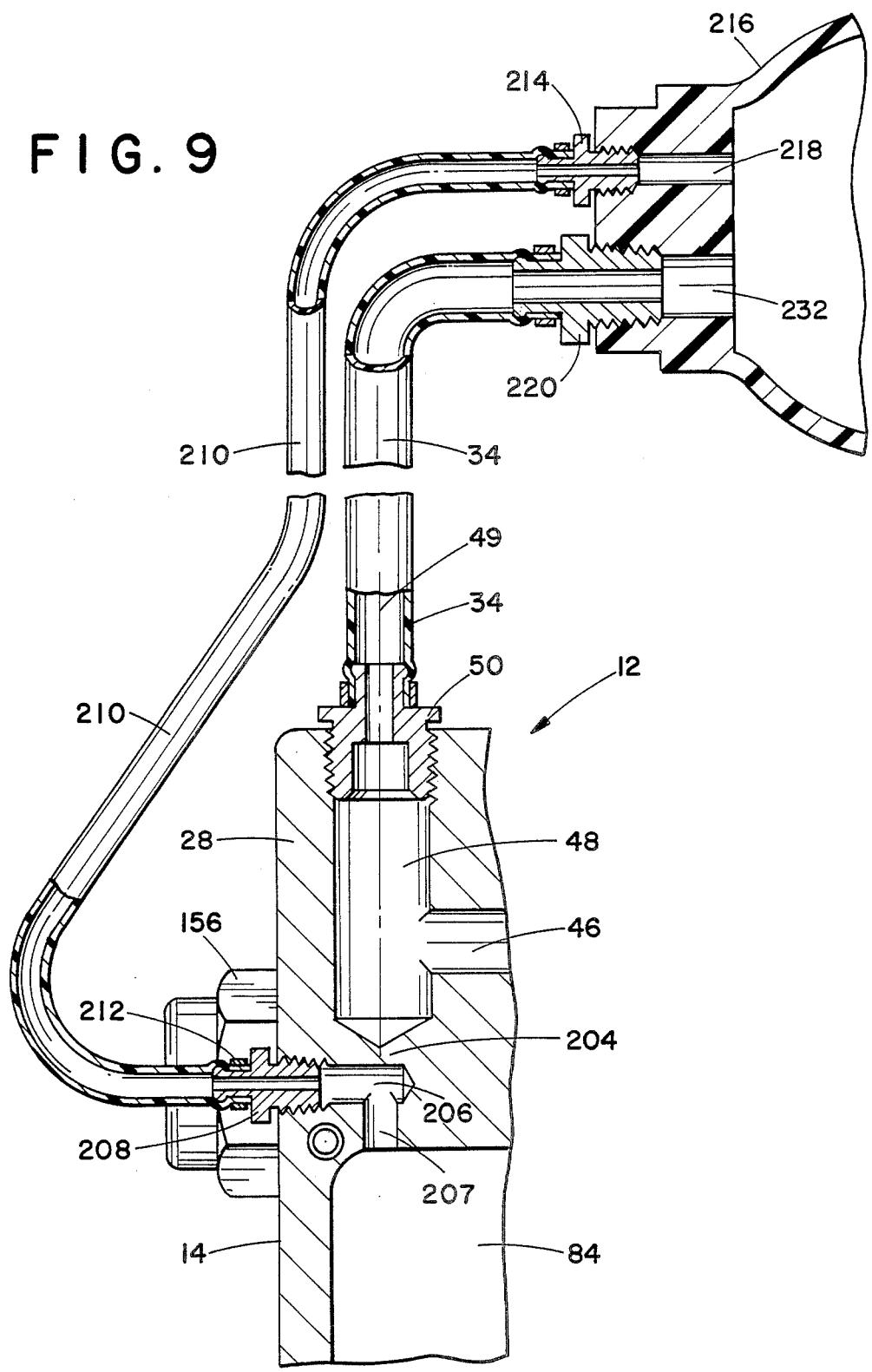
FIG. 9 is a sectional elevation view of a portion of the pressure demand valve shown in FIGS. 1-6 and showing a modification thereof in connection with another embodiment of the sensor arrangement for controlling the valve.

FIG. 9 illustrates yet another embodiment of a breathing sensor arrangement for use with the pressure demand valve illustrated and described in connection with FIGS. 1–6. Again, the pressure demand valve of this embodiment is of the same structure described hereinabove, whereby only a portion of the pressure demand valve is shown in FIG. 9, namely that portion which is modified in accordance with the present embodiment. Referring now to FIG. 9, the area 204 of body portion 12 of the housing between diaphragm chamber portion 84 and outlet passageway bores 46 and 48 is closed, and side 28 of the housing is provided with a bore 206 extending laterally thereinto and a bore 207 opening into chamber 84 from the inner end of bore 206. The outer end of bore 206 is threaded to receive a hose coupling member 208, and sensor tube 210 of the breathing sensor arrangement has one end secured to coupling 208 such as by a clamp 212. The other end of tube 210 is connected to a hose coupling 214 mounted on a face mask 216 so as to communicate the interior of the face mask with sensor tube 210 through a passageway 218 in the face mask. Breathing hose 34 is similarly coupled with face mask 216 by means of a hose coupling 220 which serves to communicate the interior of the face mask with the breathing hose through a passageway 222 in the face mask. In connection with the breathing hose and sensor tube, it will be appreciated that these components can be separate between the pressure demand valve and face mask, as shown in FIG. 9, can be separate tubes suitably secured to one another at locations along the length thereof between the pressure demand valve and face mask, or can be coextruded and separated at the opposite ends thereof to facilitate the connections to the pressure demand valve and face mask.

The breathing sensor arrangement in FIG. 9 provides a much simpler construction and coupling arrangement between the sensor tube and the pressure demand valve and face mask. As with the embodiments illustrated in FIGS. 1–8, sensor tube 210 precludes breathing gas flowing from the source to the face mask from entering diaphragm chamber 84 so as to affect the control thereof. Furthermore, operation of the pressure demand valve with the breathing sensor illustrated in FIG. 9 is the same as that described hereinabove in connection with the breathing sensor shown in FIGS. 7 and 8, except for the venturi effect realized with the latter embodiments. In connection with the embodiment of FIG. 9, by having the sensor tube 210 outside the breathing hose 34, there is less resistance to the flow of breathing gas through the breathing hose, whereby the accelerated diaphragm displacement and opening of the flow control valve provided by the venturi effect during inhalation is not necessary to achieve the desired flow rate of breathing gas to the user. It will be appreciated at the same time, that by locating the end of sensor tube 210 in the face mask, there is an immediate sensing of the user's inhaling and exhaling and thus control of the pressure in the diaphragm chamber and opening and closing of the flow control valve member.

While considerable emphasis has been placed herein on the structures and structural interrelationships between the component parts of preferred embodiments of the invention illustrated and described, it will be appreciated that other embodiments of the invention can be made and that changes can be made in the embodiments disclosed without departing from the principles of the invention. For example in this respect, it will be appreciated that the diaphragm can be round rather than rectangular and that other arrangements can be provided for selectively connecting the pressure demand valve to primary and secondary sources of breathing gas under pressure. One such connecting arrangement would include eliminating the spool sleeve and providing suitable fittings at the opposite ends of bore 32 for coupling with the supply sources. Another modification or modifications which will be obvious relate to the coupling arrangements by which the breathing hose and/or the breathing hose and sensor tube are connected to the face mask or other user utilization device with which the pressure demand valve is used. The foregoing and other modifications will be suggested or obvious from the disclosure of the preferred embodiments herein, whereby it is to be distinctly understood that the foregoing descriptive matter is to be interpreted merely as illustrative of the present invention and not as a limitation.

Having thus described the invention, it is claimed:

1. Open circuit emergency breathing apparatus adapted to be connected to a source of breathing gas under pressure and comprising, a pressure demand valve, and user utilization means including breathing hose means for directing breathing gas from said pressure demand valve to a user of the apparatus, said pressure demand valve including housing means, said housing means including flow passageway means therethrough having an inlet end and an outlet end, means on said housing means for connecting said inlet end of said passageway means to said source of breathing gas under pressure, means on said housing means for connecting said breathing hose means to said outlet end of said passageway means between said inlet and outlet ends thereof and including valve member means supported in said housing means for displacement between open and closed positions, said valve member means in said open position thereof opening said passageway means such that breathing gas can flow through said passageway means from said source through said outlet end to said user utilization means, said valve member means in said closed position thereof closing said passageway means to the flow of breathing gas therethrough from said source, said housing means including means providing a diaphragm chamber, diaphragm means mounted in said housing means and dividing said diaphragm chamber into first and second chamber portions, said second chamber portion being vented to atmosphere, said diaphragm means being displaceable between first and second positions respectively in response to decreases and increases in the pressure in said first chamber portion relative to atmospheric pressure, valve member actuator means displaced in response to displacement of said diaphragm means such that said valve member means is respectively in said open and closed positions thereof when said diaphragm means is in said first and second positions thereof, said diaphragm means having a third position between said first and second positions thereof and said valve member means having a partially open position between said open and closed positions thereof, said diaphragm means being in said third position when the pressure in said first and second chamber portions is equal and said valve member actuator means positioning said valve member means in said partially open position when said diaphragm means is in said third position, and tubular breathing sensor means connecting said first chamber portion in flow communication with said user utilization means such that the flow of breathing gas from said source to said outlet end of said passageway means is precluded from entering said first chamber portion and the inhaling and exhaling of a user respectively decreases and increases the gas pressure in said first chamber portion through said tubular breathing sensor means.

2. Breathing apparatus according to claim 1, wherein said breathing sensor means includes a tubular member in said flow passageway means between said flow control valve means and said outlet end of said passageway means, said tubular member having a first end opening into said first chamber portion and a second end in said passageway means and facing downstream with respect to the direction of flow of breathing gas from said flow control valve means to said outlet end of said passageway means.

3. Breathing apparatus according to claim 2, wherein said outlet end of said passageway means includes first and second passageways extending serially downstream from said flow control valve means with respect to said direction of flow, said second passageway having an axis and being perpendicular to and intersecting said first passageway, and said tubular member extending across said first passageway such that said second end of said tubular member is in said second passageway and coaxial therewith.

4. Breathing apparatus according to claim 1, wherein said housing means includes means for removably receiving strap means by which said pressure demand valve can be supported on the body of a user.

5. Breathing apparatus according to claim 1, wherein said means for connecting said inlet end of said passageway means to said source of breathing gas includes first and second spaced apart and structurally diverse coupling means supported by said housing means, each said coupling means being in flow communication with said inlet end of said passageway means.

6. Breathing apparatus according to claim 1, wherein said valve member means includes end means extending into said first chamber portion and said valve member actuator means includes lever means in said first chamber portion between said diaphragm means and said end means of said valve member means, said lever means displacing said valve member means to said open position thereof in response to displacement of said diaphragm means from said second to said first position thereof.

7. Breathing apparatus according to claim 6, wherein said breathing sensor means includes a tubular member in said flow passageway means between said flow control valve means and said outlet end of said passageway means, said tubular member having a first end opening into said first chamber portion and a second end in said passageway means and facing downstream with respect to the direction of flow of breathing gas from said flow control valve means to said outlet end of said passageway means.

8. Breathing apparatus according to claim 7, wherein said outlet end of said passageway means includes first and second passageways extending serially downstream from said flow control valve means with respect to said direction of flow, said second passageway having an axis and being perpendicular to and intersecting said first passageway, and said tubular member extending across said first passageway such that said second end of said tubular member is in said second passageway and coaxial therewith.

9. Breathing apparatus according to claim 8, wherein said valve member actuator means includes spring means biasing said valve member means from said open position toward said closed position thereof.

10. Breathing apparatus according to claim 9, wherein said means for connecting said inlet end of said passageway means to said source of breathing gas includes first and second spaced apart and structurally diverse coupling means supported by said housing means, each said coupling means being in flow communication with said inlet end of said passageway means.

11. Breathing apparatus according to claim 1, wherein said user utilization means includes face mask means connected to said breathing hose means and wherein said breathing sensor means connecting said first chamber portion in flow communication with said user utilization means includes sensor tube means having opposite ends, means connecting one of said opposite ends of said sensor tube means in flow communication with said first chamber portion, and means connecting the other of said opposite ends of said sensor tube means in flow communication with said face mask means.

12. Breathing apparatus according to claim 11, wherein said sensor tube means is inside said breathing hose means.

13. Breathing apparatus according to claim 12, wherein said face mask means includes coupling means having an inlet end, said breathing hose means being connected to said inlet end of said coupling means, and said means connecting the other of said opposite ends of said sensor tube means to said face mask including means supporting said other end of said sensor tube means in said inlet end of said coupling means.

14. Breathing apparatus according to claim 13, wherein said inlet end of said coupling means of said face mask means has wall means extending thereabout, said means supporting said other end of said sensor tube means including a tubular support member coaxial with said axis and having axially opposite ends, one of said opposite ends of said support member being connected to said other end of said sensor tube means, the other of said opposite ends of said support member including flange means in said inlet end of said coupling means, said flange means having an outer periphery radially spaced inwardly from said wall means of said inlet end of said coupling means to provide a peripheral gap therebetween for the flow of breathing gas through said breathing hose means to said face mask.

15. Breathing apparatus according to claim 11, wherein said sensor tube means is outside said breathing hose means.

16. Breathing apparatus according to claim 15, wherein said face mask means includes first and second flow passageways opening to the interior thereof, means connecting said breathing hose means to said first passageway, and means connecting said other end of said sensor tube means to said second passageway.

17. Breathing apparatus according to claim 1, and further including spring means in said second chamber portion biasing said diaphragm means to said third position.

18. Breathing apparatus according to claim 17, wherein said valve member actuator means includes spring means biasing said valve member means toward said closed position thereof.

19. Open circuit emergency breathing apparatus adapted to be connected to a source of breathing gas under pressure and comprising a pressure demand valve, and user utilization means including breathing hose means for directing breathing gas from said pressure demand valve to a user of the apparatus, said pressure demand valve including housing means having upper and lower portions, said upper portion providing body means, flow passageway means extending through said body means and having inlet and outlet ends, means on said housing means for connecting said inlet end of said passageway means to said source of breathing gas under pressure, means on said housing means for connecting said breathing hose to said outlet end of said passageway means, said passageway means including a vertical passageway portion between said inlet and outlet ends, flow control valve means in said passageway means including means providing a valve seat in said vertical passageway portion having a vertical axis, valve member means and means in said body means supporting said valve member means for vertical reciprocation coaxial with said seat, said valve member means having an upper end in said vertical passageway portion, said valve member means having an open position in which said upper end is spaced from said seat such that breathing gas can flow through said passageway means from said source through said outlet end to said user utilization means, said valve member means having a closed position in which said upper end engages said seat to close said passageway means to the flow of breathing gas therethrough from said source, said lower portion of said housing means including wall means extending downwardly from said body means and providing a diaphragm chamber, diaphragm means mounted on said wall means in a vertical plane in said chamber and dividing said chamber into first and second chamber portions, said second chamber portion being vented to atmosphere, said valve member means having lower end means extending into said first chamber portion, valve member actuator means including means in said first chamber portion interconnecting said lower end of said valve member means and said diaphragm means, said diaphragm means being displaceable between first and second positions respectively in response to decreases and increases in the pressure in said first chamber portion relative to atmospheric pressure and said valve member actuator means being displaced in response to displacement of said diaphragm means such that said valve member means is respectively in said open and closed positions thereof when said diaphragm means is in said first and second positions thereof, said diaphragm means having a third position between said first and second positions thereof and said valve member means having a partially open position between said open and closed positions thereof, said diaphragm means being in said third position when the pressure in said first and second chamber portions is equal and said valve member actuator means positioning said valve member means in said partially open position when said diaphragm means is in said third position, and tubular breathing sensor means connecting said first chamber portion in flow communication with said user utilization means such that the flow of breathing gas from said source to said outlet end of said passageway means is precluded from entering said first chamber portion and the inhaling and exhaling of a user respectively decreases and increases the gas pressure in said first chamber portion through said tubular breathing sensor means.

20. Breathing apparatus according to claim 19, wherein said upper portion of said housing means includes means for removably receiving strap means by which said pressure demand valve can be supported on the body of a user.

21. Breathing apparatus according to claim 19, wherein said housing means has front and back ends and laterally opposite sides, said means for connecting said inlet end of said passageway means to said source including a bore in said body portion having opposite ends opening through said opposite sides of said housing means, said inlet end of said passageway means opening into said bore between said opposite ends thereof, and coupling means at said opposite ends of said bore for selectively connecting one of said opposite ends to said source of breathing gas.

22. Breathing apparatus according to claim 21, and apertured sleeve means extending through said bore and having ends outwardly of each of said opposite ends of said bore, said coupling means including first coupling means on one end of said sleeve means and second coupling means on the other end of said sleeve means, said first and second coupling means being structurally different from one another.

23. Breathing apparatus according to claim 19, wherein said means providing a valve seat for said valve member means includes a valve seat insert removably mounted in said vertical passageway portion, said valve seat insert including tubular wall means in said vertical passageway portion coaxial with said valve seat and having upper and lower ends, said upper end of said tubular wall means being closed and said lower end thereof being open and providing said valve seat, sealing means between said tubular wall means and said vertical passageway portion dividing said passageway portion into upper and lower ends, said tubular wall means including openings therethrough communicating the interior of said tubular wall means with said upper end of said vertical passageway portion, said lower end of said tubular wall means being in said lower end of said vertical passageway portion, the part of said passageway means between said inlet end and said vertical passageway portion opening into said upper end of said vertical portion, and the part of said passageway means between said vertical passageway portion and said outlet end opening into said lower end of said vertical portion.

24. Breathing apparatus according to claim 23, wherein said body means includes a cylindrical chamber coaxial with said vertical axis of said valve seat, said cylindrical chamber opening into said lower end of said vertical passageway portion and having ann inner end spaced from said first chamber portion of said diaphragm chamber, said valve member means including a cylindrical body vertically reciprocable in said cylindrical chamber and having an inner end therein spaced from said inner end of said cylindrical chamber when said valve member means is in said open and closed positions thereof, said valve member means having port means extending through said cylindrical body from said upper end of said valve member means and opening into said cylindrical chamber between said inner ends of said cylindrical chamber and cylindrical body, and said port means opening to the interior of said tubular wall means at said upper end of said valve member means, whereby breathing gas under pressure from said source can flow through said port means into said cylindrical chamber to bias said upper end of said valve member means toward said valve seat.

25. Breathing apparatus according to claim 24, wherein said valve member means further includes a stem extending downwardly from said cylindrical body and into said first chamber portion to provide said lower end means of said valve member means, and said valve member actuator means includes lever means in said first chamber portion having a first end pivotally connected to said stem and a second end slidably engaging said diaphragm means.

26. Breathing apparatus according to claim 25, and further including spring means in said second chamber portion biasing said diaphragm means to said third position.

27. Breathing apparatus according to claim 26, wherein said valve member actuator means includes spring means in said cylindrical chamber between said inner end thereof and said inner end of said cylindrical body of said valve member means biasing said valve member means toward said closed position thereof.

28. Breathing apparatus according to claim 27, wherein said outlet end of said passageway means includes a cylindrical outlet port having an axis and said breathing sensor means includes a tubular member mounted in said body means and having opposite ends, one of said ends of said tubular member opening into said first chamber portion of said diaphragm chamber, and the other of said opposite ends of said tubular member being coaxial with and extending into said outlet port.

29. Breathing apparatus according to claim 28, wherein said body means has a top end and said outlet port opens through said top end, whereby said axis of said outlet port is vertical, said outlet port having an inner end, said passageway means between said flow control valve means and said outlet end including a portion opening laterally into said outlet port at said inner end thereof, and said tubular member being linear between said opposite ends thereof.

30. Breathing apparatus according to claim 29, wherein said housing means has front and back ends and laterally opposite sides, said means for connecting said inlet end of said passageway means to said source including a bore in said body portion having opposite ends opening through said opposite sides of said housing means, said inlet end of said passageway means opening into said bore between said opposite ends thereof, and coupling means at said opposite ends of said bore for selectively connecting one of said opposite ends to said source of breathing gas.

31. Breathing apparatus according to claim 30, and further including apertured sleeve means extending through said bore and having ends outwardly of each of said opposite ends of said bore, said coupling means including first coupling means on one end of said sleeve means and second coupling means on the other end of said sleeve means, said first and second coupling means being structurally different from one another.

32. Breathing apparatus according to claim 31, wherein said upper portion of said housing means includes means for removably receiving strap means by which said pressure demand valve can be supported on the body of a user.

33. Breathing apparatus according to claim 27, wherein said user utilization means includes face mask means connected to said breathing hose means and wherein said breathing sensor means connecting said first chamber portion in flow communication with said user utilization means includes sensor tube means having opposite ends, means connecting one of said opposite ends of said sensor tube means in flow communication with said first chamber portion, and means connecting the other of said opposite ends of said sensor tube means in flow communication with said face mask means.

34. Breathing apparatus according to claim 33, wherein said sensor tube means is inside said breathing hose means.

35. Breathing apparatus according to claim 34, wherein said face mask means includes coupling means having an inlet end, said breathing hose means being connected to said inlet end of said coupling means, and said means connecting the other of said opposite ends of said sensor tube means to said face mask means including means supporting said other end of said sensor tube means in said inlet end of said coupling means.

36. Breathing apparatus according to claim 35, wherein said housing means has front and back ends and laterally opposite sides, said means for connecting said inlet end of said passageway means to said source including a bore in said body portion having opposite ends opening through said opposite sides of said housing means, said inlet end of said passageway means opening into said bore between said opposite ends thereof, and coupling means at said opposite ends of said bore for selectively connecting one of said opposite ends to said source of breathing gas.

37. Breathing apparatus according to claim 36, wherein said upper portion of said housing means includes means for removably receiving strap means by which said pressure demand valve can be supported on the body of a user.

38. Breathing apparatus according to claim 33, wherein said sensor tube means is outside said breathing hose means.

39. Breathing apparatus according to claim 38, wherein said housing means has front and back ends and laterally opposite sides, said means for connecting said inlet end of said passageway means to said source including a bore in said body portion having opposite ends opening through said opposite sides of said housing means, said inlet end of said passageway means opening into said bore between said opposite ends thereof, and coupling means at said opposite ends of said bore for selectively connecting one of said opposite ends to said source of breathing gas.

40. Breathing apparatus according to claim 39, wherein said upper portion of said housing means includes means for removably receiving strap means by which said pressure demand valve can be supported on the body of a user.

41. A pressure demand valve for use with open circuit emergency breathing apparatus including a source of breathing gas under pressure and use utilization means including a breathing hose, said pressure demand valve including housing means, said housing means including flow passageway means therethrough having an inlet end and an outlet end, means on said housing means for connecting said inlet end of said passageway means to a source of breathing gas under pressure, means on said housing means for connecting a breathing hose to said outlet end of said passageway means, flow control valve means in said passageway means between said inlet and outlet ends thereof and including valve member means supported in said housing means for displacement between open and closed positions, said valve member means in said open position thereof opening said passageway means such that breathing gas can flow through said passageway means from said source through said outlet end, said valve member means in said closed position thereof closing said passageway means to the flow of breathing gas therethrough from said source, said housing means including means providing a diaphragm chamber, diaphragm means mounted in said housing means and dividing said diaphragm chamber into first and second chamber portions, said second chamber portion being vented to atmosphere, said diaphragm means being displaceable between first and second positions respectively in response to decreases and increases in the pressure in said first chamber portion relative to atmospheric pressure, valve member actuator means displaced in response to displacement of said diaphragm means such that said valve member means is respectively in said open and closed positions thereof when said diaphragm means is in said first and second positions thereof, and diaphragm means having a third position between said first and second portions thereof and said valve member means having a partially open position between said open and closed positions thereof, said valve member actuator means positioning said valve member means in said partially open position when said diaphragm means is in said third position, said diaphragm means being in said third position when the pressure in said first and second chamber portions is equal, and means for connecting said first chamber portion in flow communication with said user's utilization means such that the flow of breathing gas from said source to said outlet end of said passageway means is precluded from entering said first chamber portion.

42. A pressure demand valve according to claim 41, and further including spring means biasing said valve member means toward closed position thereof and diaphragm spring means biasing said diaphragm means to said third position.

43. A pressure demand valve according to claim 41, wherein said means for connecting said first chamber portion in flow communication with said user utilization means includes a tubular member in said flow passageway means between said flow control valve means and said outlet end of said passageway means, said tubular member having a first end opening into said first chamber portion and a second end in said passageway means and facing downstream with respect to the direction of flow of breathing gas from said flow control valve means to said outlet end of said passageway means.

44. A pressure demand valve according to claim 43, wherein said outlet end of said passageway means includes first and second passageways extending serially downstream from said flow control valve means with respect to said direction of flow, said second passageway having an axis and being perpendicular to and intersecting said first passageway, and said tubular member extending across said first passageway such that said second end of said tubular member in in said second passageway and coaxial therewith.

45. A pressure demand valve according to claim 41, wherein said means for connecting said inlet end of said passageway means to said source of breathing gas includes first and second spaced apart and structurally diverse coupling means supported by said housing means, each said coupling means being in flow communication with said inlet end of said passageway means.

46. A pressure demand valve according to claim 41, wherein said housing means has upper and lower portions, said upper portion providing body means, said flow passageway means extending through said body means and including a vertical passageway portion between said inlet and outlet ends and having a vertical axis, said flow control valve means including means providing a valve seat for said valve member means coaxial with said vertical axis, means in said body means supporting said valve member means for vertical reciprocation coaxial with said seat, said valve member means having an upper end in said passageway portion spaced from said seat when said valve member means is in said open position and engaging said seat when said valve member means is in said closed position, said lower portion of said housing means including wall means extending downwardly from said body means and providing said diaphragm chamber, said diaphragm means being mounted on said wall means in a vertical plane in said chamber, said valve member means having lower end means extending into said first chamber portion, and said valve member actuator means including means in said first chamber portion interengaging said lower end means of said valve member means and said diaphragm means.

47. A pressure demand valve according to claim 46, wherein said upper portion of said housing means includes means for removably receiving strap means by which said pressure demand valve can be supported on the body of a user.

48. A pressure demand valve according to claim 46, wherein said housing means has front and back ends and laterally opposite sides, said vertical plane being perpendicular to said laterally opposite sides, said means for connecting said inlet end of said passageway means to said source including a bore in said body portion having opposite ends opening through said laterally opposite sides of said housing means, said inlet end of said passageway means opening into said bore between said opposite ends thereof, and coupling means at said opposite ends of said bore for selectively connecting one of said opposite ends to said source of breathing gas.

49. A pressure demand valve according to claim 48, and further including apertured sleeve means extending through said bore and having ends outwardly of each of said opposite ends of said bore, said coupling means including first coupling means on one end of said sleeve means and second coupling means on the other end of said sleeve means, said first and second coupling means being structurally different from one another.

50. A pressure demand valve according to claim 46, wherein said means providing a valve seat for said valve member means includes a valve seat insert removably mounted in said vertical passageway portion, said valve seat insert including tubular wall means in said vertical passageway portion coaxial with said valve seat and having upper and lower ends, said upper end of said tubular wall means being closed and said lower end thereof being open and providing said valve seat, sealing means between said tubular wall means and said vertical passageway portion dividing said passageway portion into upper and lower ends, said tubular wall means including openings therethrough communicating the interior of said tubular wall means with said upper end of said vertical passageway portion, said lower end of said tubular wall means being in said lower end of said vertical passageway portion, the part of said passageway means between said inlet end and said vertical passageway portion opening into said upper end of said vertical passageway portion, and the part of said passageway means between said vertical passageway portion and said outlet end opening into said lower end of said vertical passageway portion.

51. A pressure demand valve according to claim 50, wherein said body means includes a cylindrical chamber coaxial with said vertical axis of said valve seat insert, said cylindrical chamber opening into said lower end of said vertical passageway portion and having an inner end spaced from said first chamber portion of said diaphragm chamber, said valve member means including a cylindrical body vertically reciprocable in said cylindrical chamber and having an inner end therein spaced from said inner end of said cylindrical chamber when said valve member means is in said open and closed positions thereof, said valve member means having port means extending through said cylindrical body from said upper end of said valve member means and opening into said cylindrical chamber between said inner ends of said cylindrical chamber and cylindrical body, and said port means opening to the interior of said tubular wall means at said upper end of said valve member means, whereby breathing gas under pressure from said source can flow through said port means into said cylindrical chamber to bias said upper end of said valve member means toward said valve seat.

52. A pressure demand valve according to claim 51, wherein said valve member means further includes a stem extending downwardly from said cylindrical body and into said first chamber portion to provide said lower end means of said valve member means, and said valve member actuator means includes lever means in said first chamber portion having a first end pivotally connected to said stem and a second end slidably engaging said diaphragm means.

53. A pressure demand valve according to claim 52, wherein said valve member actuator means includes spring means in said cylindrical chamber between said inner end thereof and said inner end of said cylindrical body of said valve member means biasing said valve member means toward said closed position thereof.

54. A pressure demand valve according to claim 53, wherein said upper portion of said housing means includes means for removably receiving strap means by which said pressure demand valve can be supported on the body of a user.

55. A pressure demand valve according to claim 53, wherein said means for connecting said first chamber portion in flow communication with said user utilization means includes a tubular member in said flow passageway means between said flow control valve means and said outlet end of said passageway means, said tubular member having a first end opening into said first chamber portion and a second end in said passageway means and facing downstream with respect to the direction of flow of breathing gas from said flow control valve means to said outlet end of said passageway means.

56. A pressure demand valve according to claim 55, wherein said outlet end of said passageway means includes first and second passageways extending serially downstream from said flow control valve means with respect to said direction of flow, said second passageway having an axis and being perpendicular to and intersecting said first passageway, and said tubular member extending across said first passageway such that said second end of said tubular member is in said second passageway and coaxial therewith.

57. A pressure demand valve according to claim 56, wherein said body means has a top end and said second passageway is vertical and opens through said top end of said body means.

58. A pressure demand valve according to claim 57, wherein said housing means has front and back ends and laterally opposite sides, said vertical plane of said diaphragm means being perpendicular to said laterally opposite sides, said means for connecting said inlet end of said passageway means to said source including a bore in said body portion having opposite ends opening through said laterally opposite sides of said housing means, said inlet end of said passageway means opening into said bore between said opposite ends thereof, and coupling means at said opposite ends of said bore for selectively connecting one of said opposite ends to said source of breathing gas.

59. A pressure demand valve according to claim 58, and further including apertured sleeve means extending through said bore and having ends outwardly of each of said opposite ends of said bore, said coupling means including first coupling means on the other end of said sleeve means, said first and second coupling means being structurally different from one another.

60. A pressure demand valve according to claim 57, wherein said upper portion of said housing means includes means for removably receiving strap means by which said pressure demand valves can be supported on the body of a user.

* * * * *